US008968380B2

(12) United States Patent
Nimgaard

(10) Patent No.: US 8,968,380 B2
(45) Date of Patent: Mar. 3, 2015

(54) DEPLOYMENT HANDLE FOR AN INTRODUCER

(75) Inventor: Lars S. Nimgaard, Koege (DK)

(73) Assignee: Cook Medical Technologies LLC, Bloomington, IN (US)

( * ) Notice: Subject to any disclaimer, the term of this patent is extended or adjusted under 35 U.S.C. 154(b) by 475 days.

(21) Appl. No.: 12/899,203

(22) Filed: Oct. 6, 2010

(65) Prior Publication Data

US 2011/0288558 A1 Nov. 24, 2011

(30) Foreign Application Priority Data

Oct. 7, 2009 (GB) .................................. 0917557.1

(51) Int. Cl.
*A61F 2/06* (2013.01)
*A61F 2/95* (2013.01)
*A61F 2/848* (2013.01)
*A61F 2/966* (2013.01)

(52) U.S. Cl.
CPC . *A61F 2/95* (2013.01); *A61F 2/848* (2013.01); *A61F 2/966* (2013.01); *A61F 2002/9505* (2013.01); *A61F 2002/9511* (2013.01); *A61F 2002/9517* (2013.01)
USPC ...... 623/1.11; 606/108; 604/159; 604/164.01

(58) Field of Classification Search
CPC ... A61F 2/95; A61F 2/848; A61F 2002/9517; A61F 2002/9505; A61F 2002/9511; A61F 2/966
USPC ................ 606/108, 191–200; 623/1.11–1.13, 623/1.2–1.23, 6.22; 604/528, 159, 164.01; 128/898, 899
See application file for complete search history.

(56) References Cited

U.S. PATENT DOCUMENTS

| 5,776,142 | A   | * | 7/1998  | Gunderson ................... 623/1.11 |
| 6,146,415 | A   | * | 11/2000 | Fitz .............................. 623/1.11 |
| 6,395,017 | B1  |   | 5/2002  | Dwyer |
| 6,402,760 | B1  |   | 6/2002  | Fedida |
| 6,599,296 | B1  | * | 7/2003  | Gillick et al. ................. 606/108 |
| 6,669,716 | B1  | * | 12/2003 | Gilson et al. ................. 623/1.11 |
| 6,866,669 | B2  |   | 3/2005  | Buzzard et al. |
| 6,872,224 | B1  | * | 3/2005  | Telxelra Moretra et al. 623/1.12 |
| 2003/0233140 | A1 | * | 12/2003 | Hartley et al. ............... 623/1.11 |
| 2004/0073289 | A1 | * | 4/2004  | Hartley ........................ 623/1.13 |
| 2004/0098079 | A1 | * | 5/2004  | Hartley et al. ............... 623/1.11 |
| 2005/0060016 | A1 |   | 3/2005  | Wu et al. |
| 2006/0286145 | A1 |   | 12/2006 | Horan et al. |

(Continued)

FOREIGN PATENT DOCUMENTS

DE 4420142 A1 12/1995
EP 1302178 A2 4/2003

(Continued)

*Primary Examiner* — Katherine Dowe
*Assistant Examiner* — Sidharth Kapoor
(74) *Attorney, Agent, or Firm* — Richard J. Godlewski; Taiwoods Lin

(57) ABSTRACT

A handle for an implant deployment device converts rotational movement into longitudinal movement in order to provide controlled release of one or more trigger wires. The handle also allows the trigger wire to be withdrawn into the device so that it does not need to be separately removed. A preferred handle includes a rotatable portion (120) and a slidable portion (122). Releasable locks (88, 188) ensure that the handle is used to carry out implant deployment steps in a specific order.

19 Claims, 22 Drawing Sheets

(56) References Cited

U.S. PATENT DOCUMENTS

| | | |
|---|---|---|
| 2007/0073389 A1* | 3/2007 | Bolduc et al. ............. 623/1.36 |
| 2007/0156224 A1* | 7/2007 | Cioanta et al. ............. 623/1.11 |
| 2007/0156225 A1 | 7/2007 | George et al. |
| 2007/0255390 A1 | 11/2007 | Ducke et al. |

FOREIGN PATENT DOCUMENTS

| | | | |
|---|---|---|---|
| EP | 1358903 | A2 | 11/2003 |
| EP | 1806114 | A2 | 7/2007 |
| WO | 9820811 | A1 | 5/1998 |
| WO | 9949808 | A1 | 10/1999 |
| WO | 0061035 | A1 | 10/2000 |
| WO | 0067675 | | 11/2000 |
| WO | 2004028399 | | 4/2004 |
| WO | 2005032425 | | 4/2005 |
| WO | 2005037142 | | 4/2005 |
| WO | 2007047023 | A2 | 4/2007 |
| WO | 2007070788 | A2 | 6/2007 |
| WO | 2008017683 | A1 | 2/2008 |
| WO | 2009001309 | A1 | 12/2008 |

* cited by examiner

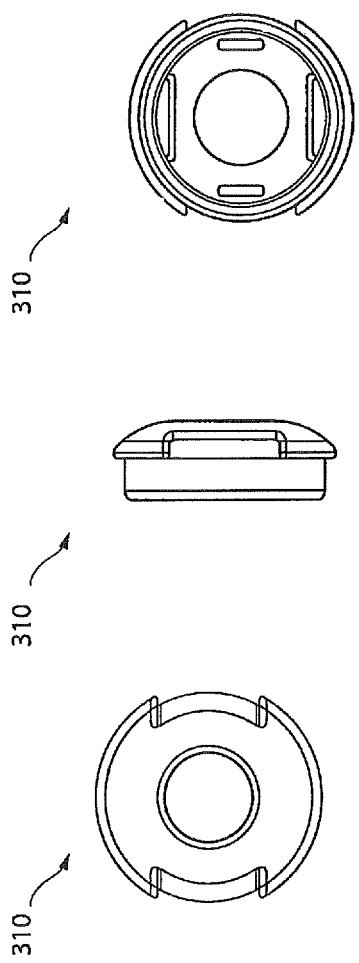

DEPLOYMENT HANDLE FOR AN INTRODUCER

TECHNICAL FIELD

The present invention relates to a deployment handle for an introducer (also referred to hereinafter as an implant deployment device), and to an introducer including such a handle.

BACKGROUND OF THE INVENTION

The use of delivery devices or introducers employing catheters has long been known for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, it has also long been known to deliver an implantable medical device by means of a catheter, often intraluminally. For example, a stent, stent-graft, vena cava filter or occlusion device may be delivered intraluminally from the femoral artery for deployment.

For procedures in which a prosthesis or other medical device is implanted into a patient, the device to be implanted is normally held on a carrier catheter or cannula of the introducer in a compressed state and then released from the carrier catheter so as to expand to its normal operating state, prior to withdrawal of the catheter from the patient to leave the implant in position.

A variety of delivery devices or introducers is known in the art. These generally involve positioning the implantable medical device on a distal part of a delivery device, that is, at an end furthest from the external manipulation end used by the clinician during the deployment procedure. The implantable medical device is normally held at the distal end of a carrier catheter of the device by a suitable restraining mechanism, which may include restraining wires or trigger wires. It is also conventional for the introducer assembly to include an outer sheath to cover the implant in order to protect the medical device and also the patient's vasculature or organs during the delivery process. Once the medical device has been positioned at the location in which it is to be released, the sheath is retracted along the carrier catheter to expose the medical device. The medical device is then expanded, either automatically, if the device is of the self-expanding type, or by a suitable expanding mechanism if not, such as by means of an expansion balloon.

Many endoluminal medical devices are radially self-expanding. Radially self-expanding devices are advantageous because they do not require complicated and bulky balloon catheter systems for deployment. Such devices present a challenge, however, in that once one end of the device is released and anchored into the body lumen, subsequent positioning can be difficult. This is particularly the case if the ends of the device include anchoring mechanisms to secure the prosthesis to the body lumen. As a consequence, many deployment devices have been proposed that allow the self-expanding medical device to be partially expanded while providing a mechanism for retaining the proximal and distal extremities of the device until the main part of the device has been properly positioned.

WO 2004/028399 discloses a stent graft deployment device for release of a distal end of a stent graft before its proximal end. The device includes a sliding handle to which the deployment catheter and a retention section or capsule are fixed mounted on a fixed handle associated with a trigger wire release mechanism. The sliding handle can slide longitudinally with respect to the fixed handle.

WO 2005/032425 discloses an introducer including a retention section for retaining a proximal end of the prosthesis thereto. The proximal end of the prosthesis is retained by a trigger-wire. The trigger-wire can be removed from the introducer to release the proximal end of the prosthesis into the body lumen.

WO 2005/037142 discloses another introducer for an expandable endovascular prosthesis. The introducer includes a retention section for retaining a proximal end of the prosthesis thereto, similar to that of WO 2005/032425.

U.S. Pat. No. 6,866,669 discloses a device for retracting an outer sheath in which there is provided, as one of two retraction mechanisms, a threaded shaft connected to the outer sheath, which can be controlled by rotation of a knurled knob.

U.S. Pat. No. 6,402,760 discloses a system which uses a motorised unit to retract a sheath.

U.S. Pat. No. 5,776,142 discloses an arrangement in which inner and outer catheters are attached to respective handle portions, which handle portions are connected to one another by means of a threaded element. Withdrawal of the sheath relative to the inner catheter is achieved by twisting the handles relative to one another.

WO 98/20811 discloses a system in which retraction of a sheath is achieved by movement of a slider in a longitudinal direction of a handle.

WO 00/67675 also discloses a longitudinally moveable actuator for withdrawing an outer sheath, provided with a locking mechanism.

DE 44 20 142 discloses a handle attached to an applicator having two guides for axial relocation of a transfer tube. One guide moves the transfer tube back. The other guide is fixed to the handle and locks the transfer tube when the first guide is moved forwards.

One problem with known deployment systems is that in order to deploy an implant correctly within a patient, different deployment steps need to be taken in a very specific order. The surgeon or clinician must be very careful to carry out the steps in the required order; mistakes could result in an abortive procedure and possible injury to a patient. Current handles include a number of components that must be removed by the surgeon during the deployment procedure. These components then need to be discarded.

SUMMARY OF THE INVENTION

The present invention seeks to provide an improved deployment handle for an introducer or deployment device and an improved introducer or deployment assembly.

According to a first aspect of the present invention there is provided a handle for an implant deployment device including: a rotatable member; and a first trigger wire release mechanism, for withdrawing a trigger wire from a portion of an implant; wherein rotation of the rotatable member causes the trigger wire release mechanism to withdraw a trigger wire so as to release a portion of an implant.

In an embodiment, the first trigger wire release mechanism is movable longitudinally with respect to the handle, the first trigger wire release mechanism being engaged with the rotatable member such that upon rotation of the rotatable member the first trigger wire release mechanism moves in a proximal direction with respect to the device.

Preferably, the first trigger wire to be released is attached to the first trigger wire release mechanism, such that movement of the first trigger wire release mechanism in a proximal direction results in withdrawal of the first trigger wire.

In a preferred embodiment, the rotatable member is substantially cylindrical and includes a lumen and an internal screw thread, wherein the first trigger wire release mechanism is substantially cylindrical and is located within the internal lumen of the rotatable member and includes an external screw thread engaged with the internal screw thread of the rotatable member, and wherein a guide member extends through the first trigger wire release mechanism to prevent rotation thereof when the rotatable member is rotated.

A stop may be provided so as to allow movement of the first trigger wire release mechanism for a limited distance in the proximal direction.

Preferably, a first releasable lock operable to prevent rotation of the rotatable member is provided.

Preferably, the first releasable lock is operable to fix the rotatable member to a non-rotatable portion of the handle in order to prevent rotation of the rotatable member.

In a preferred embodiment, the handle includes a slidable portion.

The slidable portion is preferably located distally of the rotatable member, and is able to be moved longitudinally towards the rotatable member.

In an embodiment, the slidable portion is only able to move longitudinally towards the rotatable member after movement of the first trigger wire release mechanism in a longitudinal direction.

A stop may be provided so as to allow movement of the first trigger-wire release mechanism for a limited distance in the proximal direction, wherein the slidable portion is only able to move longitudinally after the first trigger wire release mechanism has moved by said limited distance.

Preferably, movement of the slidable portion in a proximal direction disengages the stop, thereby allowing the first trigger wire release mechanism to move longitudinally in a proximal direction.

Preferably, a second trigger wire release mechanism is provided, wherein the second trigger wire release mechanism is arranged to move longitudinally in a proximal direction.

The second trigger wire release mechanism may be arranged to move longitudinally in a proximal direction only after the stop has been disengaged.

The first trigger wire release mechanism is preferably able to exert a force in a proximal direction on the second trigger wire release mechanism in order to cause the second trigger wire release mechanism to move in a proximal direction.

In a preferred embodiment, the rotatable member is substantially cylindrical and includes a lumen and an internal screw thread, the first trigger wire release mechanism is substantially cylindrical and is located within the internal lumen of the rotatable member and includes an external screw thread engaged with the internal screw thread of the rotatable member, a guide member extends through the first trigger wire release mechanism to prevent rotation thereof when the rotatable member is rotated, and the second trigger wire release mechanism is substantially cylindrical and is located within the internal lumen of the rotatable member proximal of the first trigger wire release mechanism, and the second trigger wire release mechanism does not include an external screw thread engaged with the internal screw thread of the rotatable member.

The handle may include a second releasable lock operable to prevent longitudinal movement of the slidable portion.

Preferably, the second releasable lock is operable to fix the slidable portion to a non-slidable portion of the handle in order to prevent longitudinal movement of the slidable portion.

A stop may be provided so as to allow movement of the first trigger wire release mechanism for a limited distance in the proximal direction and the second releasable lock may only be released after the first trigger wire release mechanism has moved by said limited distance.

In the preferred embodiment, the second releasable lock engages with the slidable portion of a handle and with a non-slidable portion of the handle thereby preventing relative movement therebetween, wherein in the second releasable lock engages with the longitudinal member attached to and arranged to move with the first trigger wire release mechanism such that the second releasable member cannot be released whilst engaged with the longitudinal member, whereby movement of the first trigger wire release mechanism in a proximal direction causes disengagement of the longitudinal member from the second releasable lock.

In an embodiment, the trigger wire release mechanism is arranged to rotate with a rotatable member.

Rotation of the trigger wire release mechanism may result in withdrawal of the trigger wire attached thereto.

Rotation of the trigger wire release mechanism may result in the trigger wire being wound around the trigger wire release mechanism to effect withdrawal of the trigger wire.

The trigger wire release mechanism includes a circumferential groove in which a withdrawn trigger wire may be located.

A support member may be provided distally of the trigger wire release member, the support member operable to guide the trigger wire around the trigger wire release mechanism.

According to a second aspect of the present invention, there is provided an implant deployment device including a handle as described above.

BRIEF DESCRIPTION OF THE DRAWING

Embodiments of the present invention are described below, by way of example only, with reference to the accompanying drawings, in which:

FIG. 31 is a view of the proximal end of a component of the handle of FIGS. 16 to 18;

FIG. 32 is a side view of the component of FIG. 29;

FIG. 33 is a view of the distal end of the component of FIG. 29;

DETAILED DESCRIPTION

It is to be understood that the Figures are schematic and do not show the various components to their actual scale. In many instances, the Figures show scaled up components to assist the reader in the understanding of the features disclosed therein.

In this description, when referring to an introducer or deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implantable medical device such as a stent or stent graft, the term proximal refers to a location that in use is closest to the patient's heart, in the case of a vascular implant, and the term distal refers to a location furthest from the patient's heart.

By way of introduction, and with reference to FIGS. 1 to 7, described below is the applicant's Zenith TX2® TAA Endovascular Graft and Z-Trak™ Plus Introduction System.

Figure 1:
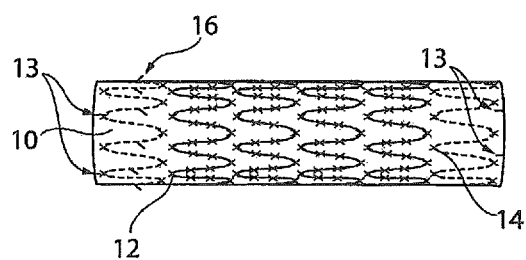
FIG. 1 illustrates a proximal component of a two-piece endovascular stent graft.
Figure 2:
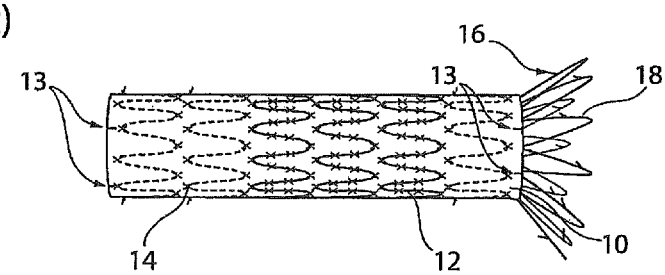
FIG. 2 illustrates a distal component of a two-piece endovascular stent graft.
Figure 3:
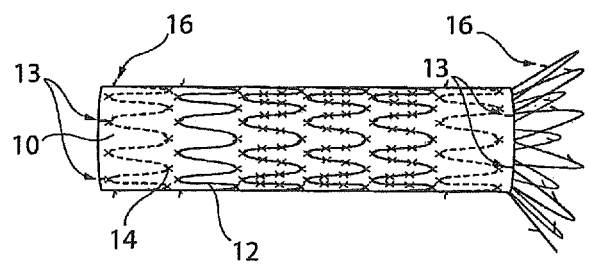
FIG. 3 illustrates a one-piece endovascular stent graft.

The Zenith TX2®TAA Endovascular Graft is a two- or one-piece cylindrical endovascular graft (the two-piece device has proximal and distal components, which are shown in FIGS. 1 and 2 respectively). The one-piece graft is shown in FIG. 3.

The stent grafts are constructed of full-thickness woven polyester fabric 10 sewn to self-expanding stainless steel Cook-Z® stents 12 with braided polyester and monofilament polypropylene suture 14.

For added fixation, the covered stent at the proximal end of the proximal component (FIG. 1) includes barbs 16, which protrude through the graft material 10. In addition, the bare stent 18 at the distal end of the distal component (FIG. 2) also includes barbs 16. The one-piece device (FIG. 3) includes both proximal and distal barbs 16.

To facilitate fluoroscopic visualisation of the stent graft, four radiopaque markers 13 are positioned on each end of the proximal and distal components and of the one-piece device.

The Zenith TX2® TAA Endovascular Graft is preloaded into the Z-Trak™ Plus Introduction System. It has a sequential deployment method to provide continuous control of the endovascular graft throughout the deployment procedure. The Z-Track™ Plus Introduction System enables precise positioning before deployment of the proximal and/or distal components and/or one-piece device.

Figure 4:
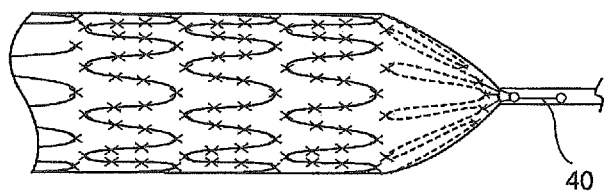
FIG. 4 shows a distal trigger-wire release mechanism.
Figure 5:
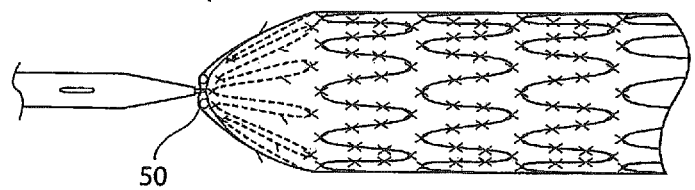
FIG. 5 shows a proximal trigger-wire release mechanism.

The main body graft components are deployed from a 20 Fr or 22 Fr Z-Trak™ Plus Introduction System. These systems use either a single trigger-wire release mechanism (proximal component) or dual trigger-wire release mechanisms (distal component and one-piece device) to secure the endovascular graft onto the delivery system until released by the physician. FIGS. 4 and 5 illustrate the distal trigger-wire attachment 40 and the proximal trigger wire attachment 50 respectively.

To facilitate sheath withdrawal, each graft component is kept in a longitudinally stretched condition on the delivery system by locking trigger wires. These trigger-wires work in tandem to deliver sequential controlled release of the Zenith TX2® TAA Endovascular Graft during deployment (see FIGS. 4 and 5).

Figure 6:
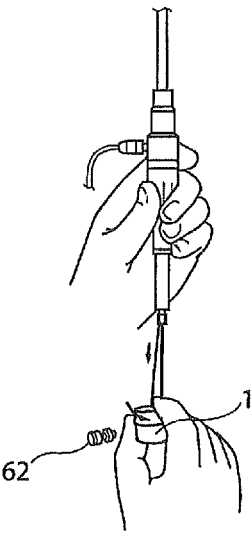
FIG. 6 illustrates a deployment system for the proximal component of FIG. 1.

FIG. 6 illustrates the external manipulation section of the Z-Trak™ Plus Introduction System for delivery of a Zenith TX2® TAA Endovascular Graft Proximal Component. As indicated above, the proximal component is loaded at the distal end (not shown) of the introducer system. The introducer system includes a trigger-wire release knob 1 having a safety screw 62. The trigger-wire release knob 1 is attached to the trigger-wire attachments 40, 50 (see FIGS. 4 and 5) that restrains the distal and proximal ends of the proximal component to the introducer. As indicated above, the proximal component is restrained on the device by a single trigger-wire release mechanism.

In order to deploy the proximal component in a patient, the introducer is firstly inserted through the patient's vasculature until its distal end reaches the site of the deployment. A sheath (not shown) is withdrawn to uncover the proximal component and allow it to expand. Whilst the central portion of the proximal component is able to expand, the proximal and distal ends remain in a constrained configuration by means of the trigger-wire attachments 40, 50.

The surgeon or clinician then loosens the safety screw 62 which enables removal of the trigger-wire release knob 1 and withdrawal and subsequent removal of the trigger-wire. As the trigger-wire is withdrawn, the proximal end of the proximal component is released from the deployment device. Further withdrawal of the trigger-wire subsequently releases the distal attachment 40 from the introducer. It is important that all of the trigger wires are removed prior to withdrawal of the delivery device.

For deployment of the distal component of the two-piece graft and for deployment of the one-piece graft, it is advantageous to deploy the distal end of the component prior to its proximal end. This is in order to avoid the "windsock" effect caused by blood flow from the proximal to the distal direction. For this reason, the distal component and the one-piece graft are restrained by a dual trigger-wire release mechanism (as indicated above).

Figure 7:
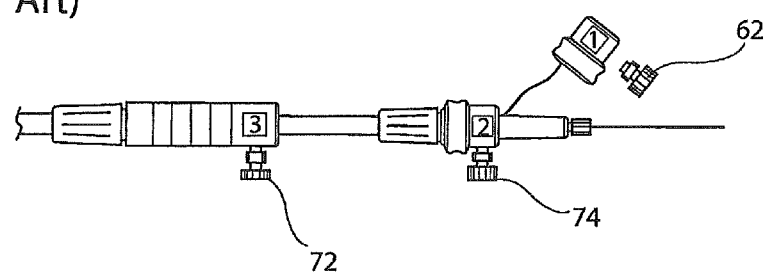
FIG. 7 illustrates a deployment system for the distal component of FIG. 2 or the one-piece stent graft of FIG. 3.

FIG. 7 illustrates the Z-Trak™ Plus Introduction System for delivery of the distal component or of a one-piece graft. To deploy the distal component or a one-piece graft as illustrated in FIGS. 2 and 3 above, the deployment device illustrated in FIG. 7 is introduced into a patient to the site of deployment. The sheath (not shown) is partially withdrawn to allow the central section of the graft to expand. Although the middle section of the graft expands, the proximal and distal ends are restrained on the deployment device. Furthermore, the distal end of the distal component or one-piece graft remains within the sheath or a retaining collar where provided.

As indicated above, the distal end of the distal component or the one-piece graft is released first. In order to do this, the surgeon or clinician releases the safety screw 62, which allows removal of the trigger-wire release mechanism 1 and its associated trigger-wire. The distal end of the distal component or one-piece graft is thus released from the introducer but is still retained within the distal end of the sheath or retaining collar. The next step is to release a safety screw 72 located on a telescoping handle 2 to which the sheath or retaining collar is attached. This allows the telescoping handle to be withdrawn in a proximal direction thereby further withdrawing the sheath or retaining collar from the distal end of the distal component or one-piece graft. The distal end of the distal component or one-piece graft is then thus fully released.

In order to deploy the proximal end of the distal component or one-piece graft, the next step is to release the proximal trigger-wire attachment 50, which is attached to a proximal trigger-wire release mechanism 3. A proximal trigger wire safety screw 74 is released, then the proximal trigger-wire release mechanism 3 is removed from the device along with its associated trigger-wire. This allows the proximal end of the distal component or one-piece graft to expand fully.

The introducer can then be removed from the patient. Once again, it is important to make sure that all trigger-wires are removed prior to withdrawal of the delivery system. As the trigger wires may be approximately 1 meter in length, this can be quite awkward. It can be seen from the above that the order of the steps taken to remove the various trigger wire release mechanisms is very important to ensure correct positioning and deployment of the stent graft.

A first embodiment of an improved handle for trigger wire release is now described with reference to FIGS. 8 to 11. The handle of the first embodiment is particularly intended for deploying the proximal component of a two-piece graft system such as that described above, but other uses may be envisaged.

The handle includes a stationary section 80 and a rotatable section 82. The stationary section 80 includes a threaded connector 84 for attaching the handle to an implant deployment device. The stationary section 80 has proximal and distal portions connected by a longitudinal portion 86, which extends along the longitudinal axis of the rotatable section 82, internally of the rotatable section 82.

The rotatable section 82 has a generally cylindrical shape which has a slight oval or rounded outer contour. It is arranged between the proximal and distal portions of the stationary section 80 of the handle. The longitudinal portion 86 of the stationary section 80 of the handle extends through a lumen of the rotatable section 82. The internal wall of the rotatable section 82 is provided with a screw thread 90, the purpose of which is described below.

Figure 10:
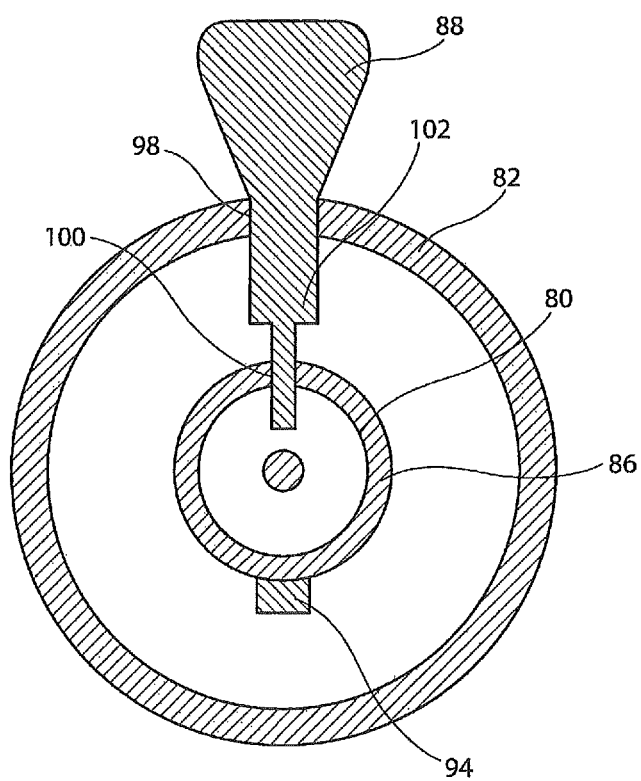
FIG. 10 shows a transverse cross-section through the line A-A of FIG. 9.
Figure 11:
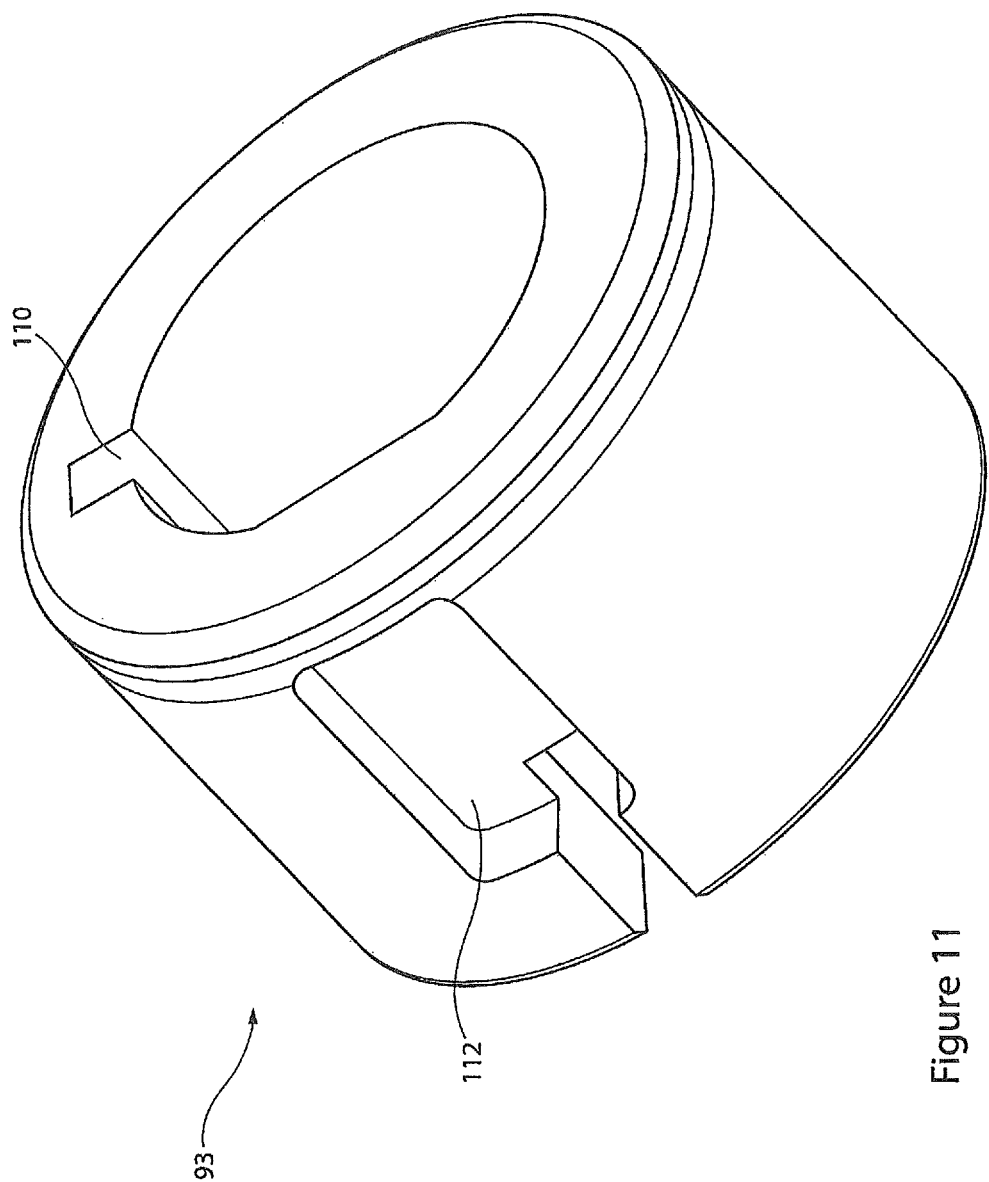
FIG. 11 is a perspective view of a component of the handle of FIG. 8.
Figure 12:
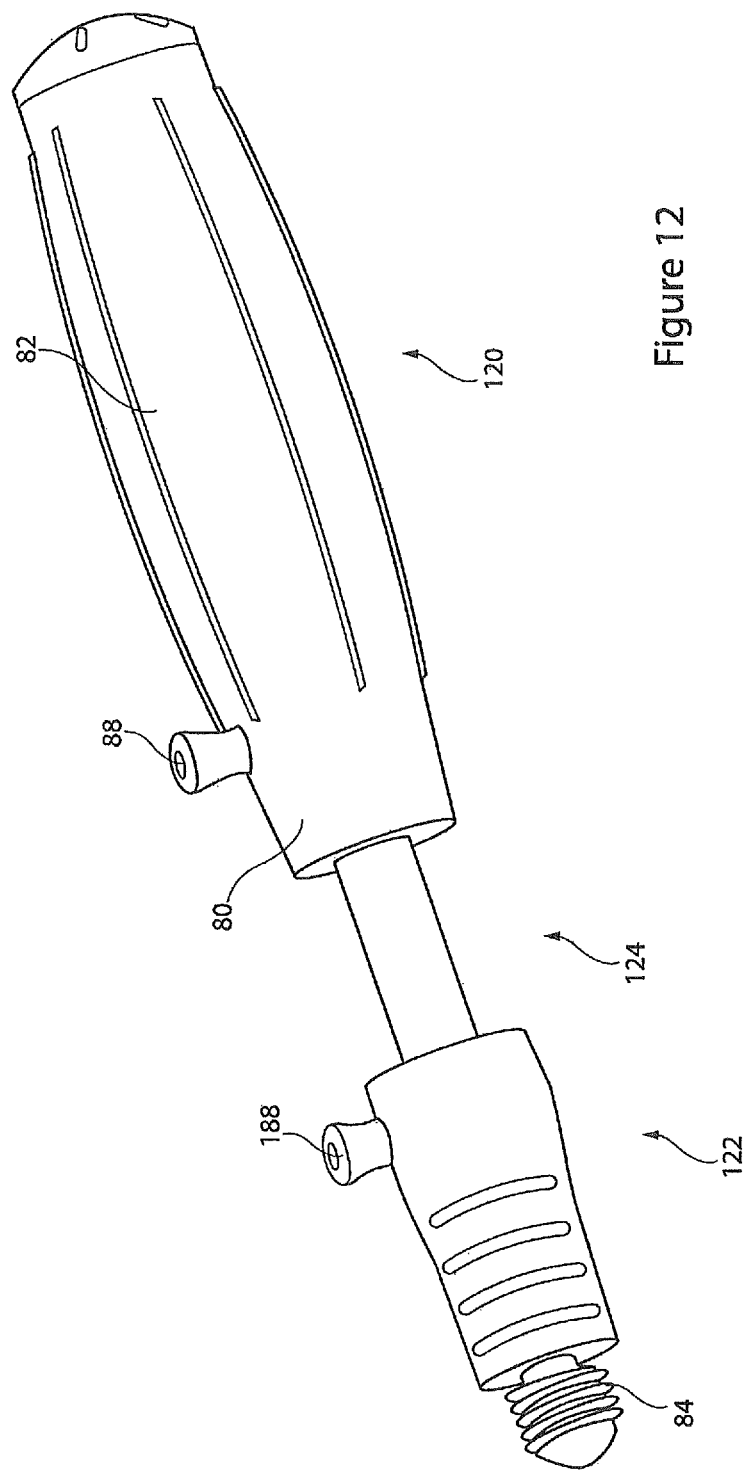
FIG. 12 is a perspective view of a second embodiment of a handle.

As can be best seen in FIG. 10, the longitudinal portion 86 of the stationary section 80 of the handle is provided with an aperture 100. Aligned with the aperture 100, there is provided an aperture 98 in the wall of the rotatable section 82 of the handle. The aperture 98 accommodates a thumb screw, or pin, 88. The thumb screw 88 has a head portion that can be manipulated by the physician in order to rotate the thumb screw 88. The thumb screw 88 also includes a tail portion 102 that extends through the aperture 98 and extends towards the longitudinal portion 86 of the stationary section 80 of the handle. The end of the tail portion 102 of the thumb screw 88 extends through the aperture 100 in the longitudinal portion 86 of the stationary section 80 of the handle.

Figure 9:
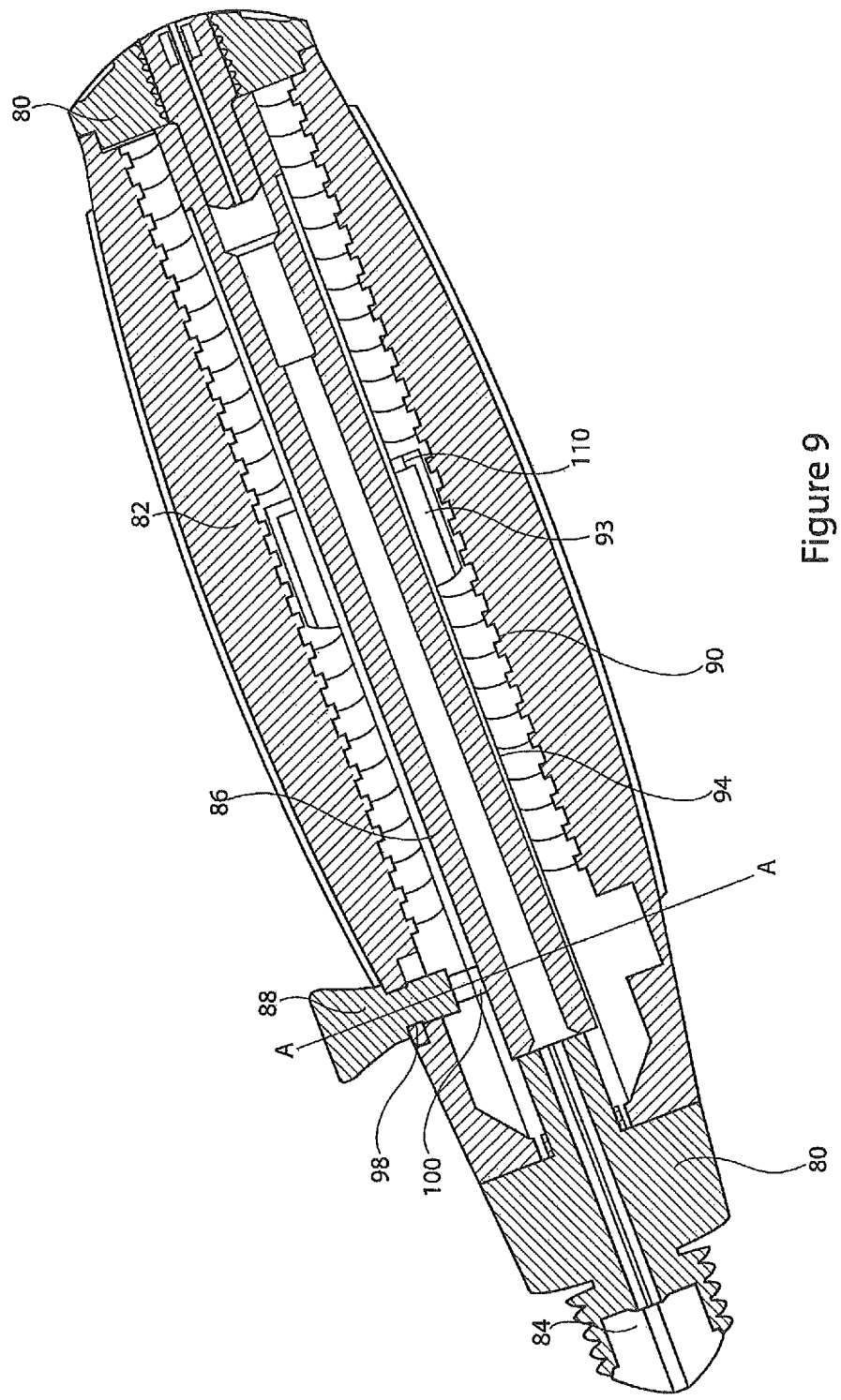
FIG. 9 shows a longitudinal cross-section of the handle of FIG. 8.

A bushing 93 is provided within the lumen of the substantially cylindrical rotatable section 82 of the handle. The bushing 93 can be seen in greater detail in FIG. 11. As shown in FIG. 9, the bushing 93 is arranged radially around the longitudinal portion 86 of the stationary section 80 of the handle.

The bushing 93 includes a notch 110 in its inner wall. The notch 110 engages with a guide rod 94 running longitudinally through the handle. The outer wall of the bushing 93 includes a recess 112 to which a trigger wire that retains the proximal and distal ends of a proximal component of a two-piece stent graft (see FIGS. 4 and 5) is attached in a suitable manner. An outer tubing (not shown) may be provided to hold the trigger wire in place. Although not shown, the bushing 93 is provided with a threading on its outer wall to engage with the threading 90 provided in the handle.

The above-described handle is particularly envisaged for use in deployment of the proximal component of a two-piece stent graft as illustrated in FIG. 1. The proximal component is introduced to the desired site of deployment within a patient in the usual manner. The sheath retaining the proximal component in its compressed configuration is withdrawn, which allows the central section of the proximal component to expand as described above. A single trigger wire is used to retain both the proximal and distal ends of the proximal component to the deployment device as illustrated in FIGS. 4 and 5. The above-described handle is then used to release the trigger wire as follows.

Figure 8:
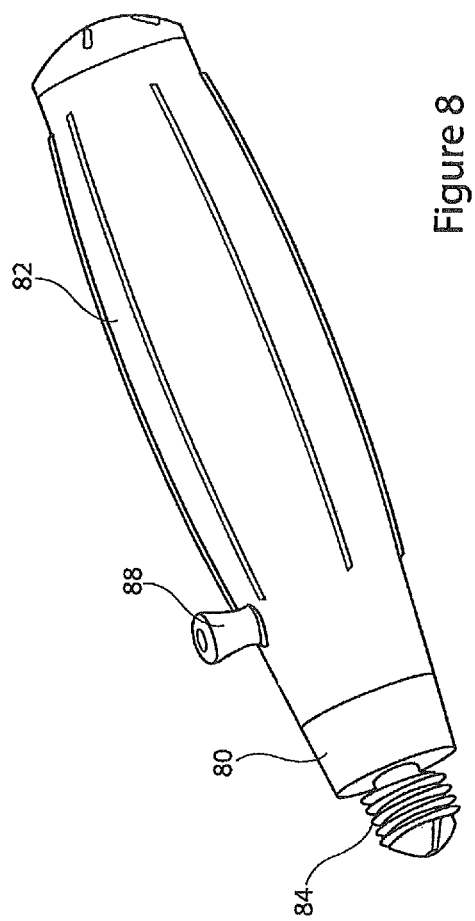
FIG. 8 is a perspective view of a first embodiment of a handle.

Firstly, it is to be noted that the rotatable part 82 of the handle as shown in FIGS. 8 to 10 cannot be rotated. This is because the thumb screw 88 is engaged with the apertures 98, 100. This therefore locks the stationary part of the handle to the rotatable part of the handle. Thus, any attempt to rotate the rotatable section 82 of the handle is blocked. Therefore, the first step to be taken by the surgeon is to release the thumb screw 88. Once this has been released, rotation is possible.

As the rotatable part 82 of the handle is rotated with respect to the stationary part 80 of the handle, the bushing 93 to which the trigger wire is attached moves in a proximal direction due to its engagement with the threading 90. The bushing 93 is itself prevented from rotating by engagement with the rod 94 along which it slides. As the bushing 93 moves in a proximal direction, the release wires attached thereto are pulled also in a proximal direction thereby releasing the stent graft.

Continued rotation of the rotatable part 82 of the handle causes the bushing 93 to move to the proximal-most end of the handle. As it does so, the trigger wire is pulled into the deployment catheter; further discarding of the trigger wire is thus unnecessary.

The above-described handle provides many advantages over current designs. Deployment is very controlled since rotation of the rotatable section 82 of the handle is converted into a very small amount of translational movement of the bushing 93 in the proximal direction. Therefore, there is no sudden movement when friction is overcome: the movement is substantially continuous. This results in more precise control, and also in the surgeon needing to apply less force to effect withdrawal of the trigger wire or wires. As indicated above, a further advantage is that withdrawal of the trigger wire into the catheter means that this can be removed from the patient at the same time as removal of the implant deployment device itself.

Many modifications to the above-described embodiment may be made. For example, the handle could be modified to withdraw also a sheath covering the medical device. The skilled person will readily be able to determine an appropriate coupling of the handle mechanism to the sheath assembly form the teachings herein and common general knowledge.

A second embodiment of a handle 41 is described with reference to FIGS. 12 to 15. The second embodiment is particularly envisaged for deploying the distal component of a two-piece graft system such as that described above (see FIG. 2), or for deploying a one-piece graft as described above (see FIG. 3). It is particularly useful where one end (for example, the distal end) of a graft should be deployed prior to the proximal end.

The second embodiment is in many respects similar to the first embodiment described above with reference to FIGS. 8 to 11. However, this embodiment of the handle includes two separate handle portions 120, 122. The two handle portions 120, 122 are axially aligned such that one of the handle portions 120 (hereinafter referred to as the rotatable portion 120) is arranged proximally of the other handle portion 122 (hereinafter referred to as the slidable portion 122). The rotatable portion 120, in particular, is similar to the handle of the first embodiment described above, in that it includes a stationary section 80 and a rotatable section 82. There is provided, however, an overlap between the walls of the stationary section 80 and the rotatable section 82.

The rotatable portion 120 also includes a bushing 93 (hereinafter referred to as the second bushing 93) arranged radially around the longitudinal portion 86 of the stationary section 80. The trigger wires restraining the ends of the stent graft (see FIGS. 4 and 5) are attached to the second bushing 93. However, the second bushing 93 of the second embodiment does not include an external thread. Instead it is able to slide within the rotatable portion 120 of the handle. It is sized to have an interference fit within the rotatable portion 120 of the handle, thus requiring some force from another component in order to be able to move.

The rotatable portion 120 of the second embodiment also includes a first bushing 193. This does include an external thread 130, as can best be seen in FIG. 13. This mates with the threading 90 provided on the internal wall of rotatable section 82 of the rotatable portion 120 of the handle. The first bushing 193 includes a longitudinal groove extending through its wall, the purpose of which will be described below.

As with the first embodiment of the handle, the rotatable portion 120 of the handle includes a thumbscrew 88, or alternatively a pin, hereinafter referred to as a first safety screw 88. The first safety screw 88 extends through an aperture 98 within the wall of the rotatable section 82 of the rotatable portion 120 of the handle, and also through an aligned aperture 198 provided in the wall of the stationary section 80 of the rotatable portion 120 of the handle. The aligned apertures are provided within the region of overlap between the stationary section 80 and the rotatable section 82.

Extending from the distal end of the rotatable portion 120 of the handle is a middle portion 124 that connects the rotatable portion 120 with the slidable portion 122. The middle portion 124 is generally cylindrical in shape, but includes opposed flat surfaces on its external wall, the purpose of which will be described below. The middle portion 124 also includes an indentation 134, which in this embodiment is circular. This can best be seen in FIG. 14. The purpose of the indentation 134 is described below. The middle portion 124 is coaxial with the longitudinal portion 86 of the stationary section 80 of the rotatable portion 120 of the handle. The middle portion 124 extends partially into a lumen of the slidable portion 122 of the handle, to provide a small overlap between these portions.

Figure 13:
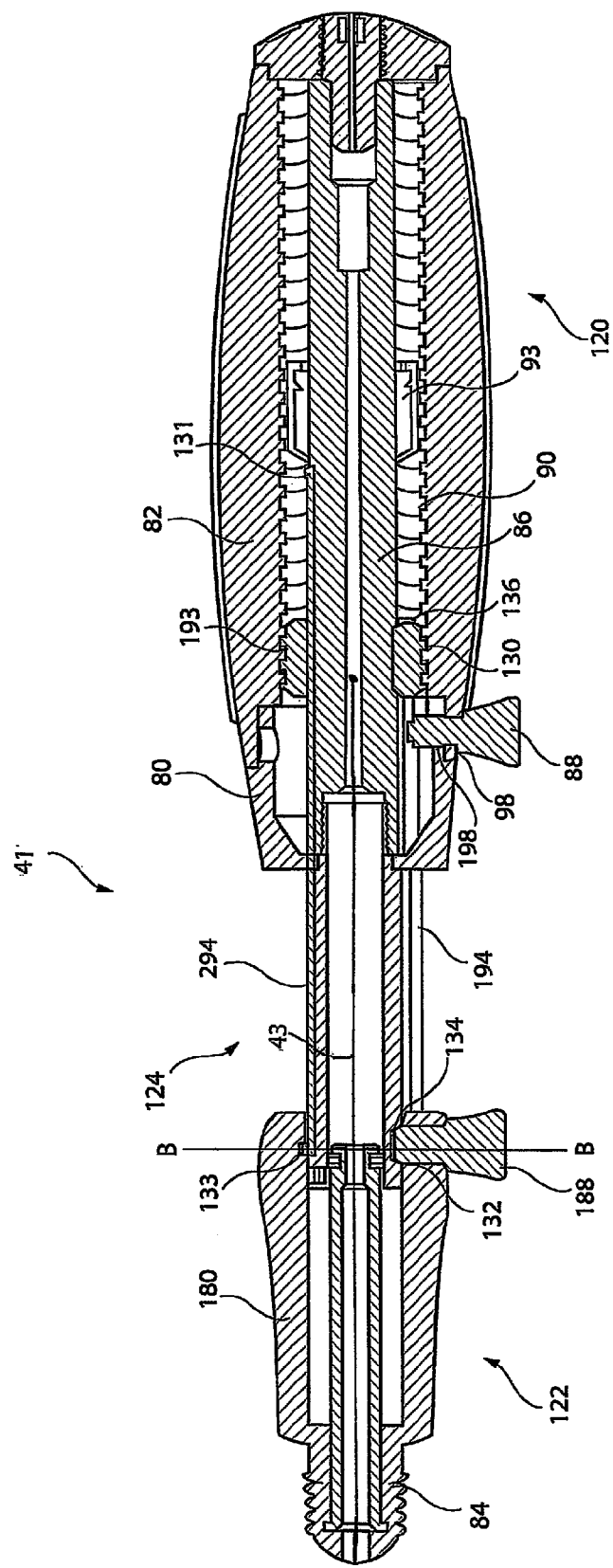
FIG. 13 shows a longitudinal cross-section of the handle of FIG. 12.
Figure 14:
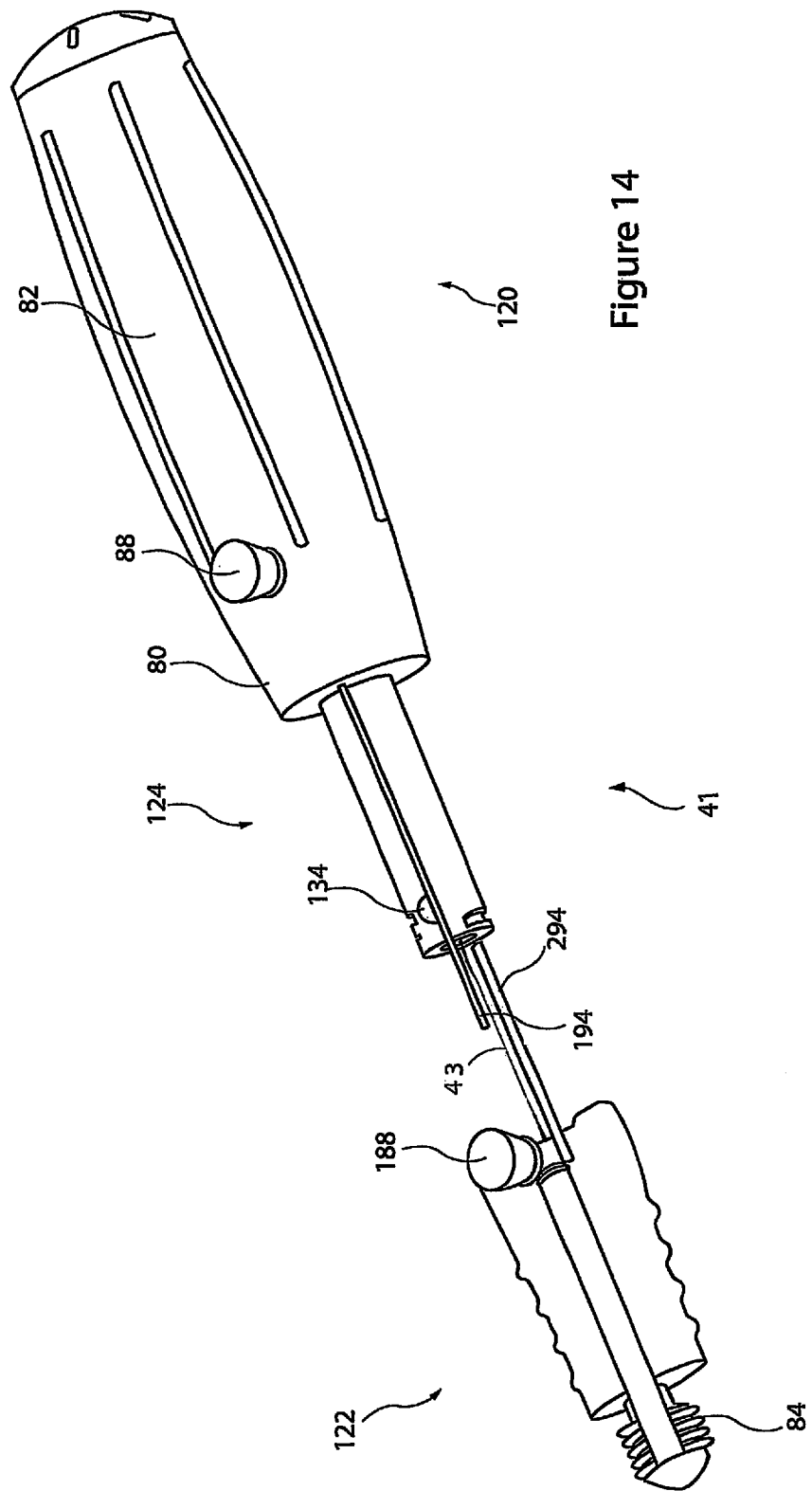
FIG. 14 is a partially exploded view of the handle of FIG. 12.
Figure 15:
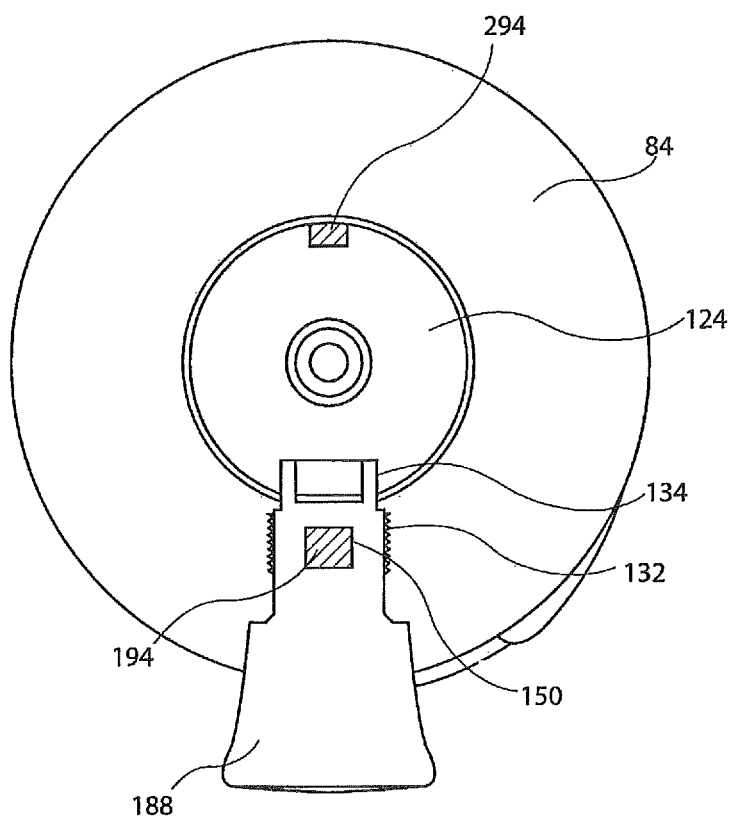
FIG. 15 shows a transverse cross-section through the line B-B of FIG. 13.

The slidable portion 122 of the handle includes a threaded connector 84 at its distal end for attaching the handle to an implant deployment device or introducer. It also includes an aperture 132 within in its wall in the region of overlap between the slidable portion 122 and the middle portion 124. The aperture 132 can be aligned with the indentation 134 provided in the middle portion 124 of the handle. A thumbscrew 188, alternatively a pin, hereinafter referred to as the second safety screw 188, is shown in FIG. 13 as engaged through the aperture 132 and into the indention 134. The second safety screw 188 includes a threading which engages with threading provided in the aperture 132. This can best be seen in FIG. 15. The second safety screw 188 further includes a aperture 150 for receiving a first safety rod 194.

The first safety rod 194 can best be seen in FIG. 13. It includes a shoulder 136 at its proximal end, which engages with the proximal face of the first bushing 193. The first safety rod 194 extends through the longitudinal groove provided in the first bushing 193 and extends distally from the rotatable portion 120 of the handle towards the slidable portion 122 of the handle. The distal end of the first safety rod 194 extends through the aperture 150 of the second safety screw 188 (see FIG. 15).

A second safety rod 294 is also provided in this second embodiment of the handle. The second safety rod 294 extends along one of the flat surfaces of the middle portion 124 of the handle and continues along the longitudinal portion 86 of the stationary section 80 of the rotatable portion 120 of the handle. The second safety rod 294 includes shoulders 131, 133 at proximal and distal ends respectively. The distal shoulder 133 engages with an indentation in the internal wall of the slidable portion 122 of the handle. The second safety rod 294 extends through the lumen of the first bushing 193, and its purpose is described in greater detail below.

It can be seen by the described arrangement of the components of the handle of the second embodiment, and as illustrated in the Figures, that the safety screws 88, 188 respectively prevent rotation of the rotatable section 82 of the rotatable portion 120 of the handle, and also prevent axial movement of the slidable portion 122 of the handle with respect to the rotatable portion 120 of the handle. In particular, it can be seen, firstly, that the first safety screw 88 prevents rotation of the rotatable section 82 of the rotatable portion 120 of the handle with respect to the stationary section 80 due to its engagement with the apertures 98, 198 provided in the respective sections of the rotatable portion 120 of the handle in the region of overlap. Engagement of the second safety screw 188 with the aperture 132 and the indentation 134 prevents sliding of the slidable portion 122 of the handle along the middle portion 124.

As indicated above, the second safety screw 188 is provided with a threading, and thus the second safety screw 188 must be rotated in order to be removed. However, in the situation illustrated in the Figures, rotation of the second safety screw 188 is prevented due to engagement of the first safety rod 194 in the aperture 150 of the second safety screw 188.

The first safety rod 194 must be removed from the aperture 150 before the second safety screw 188 can be removed: The first safety rod 194 is removed from the aperture 150 by rotating the rotatable section 82 of the rotatable portion 120 of the handle to cause movement in a proximal direction of the first bushing 193, and thus also of the first safety rod 194, which is engaged therewith by means of the shoulder 136. In order to allow this rotation, the surgeon must remove the first safety screw 88 from the apertures 98, 198 with which it is engaged.

In use, a distal component of a two-piece stent graft as illustrated in FIG. 2, or a one-piece stent graft as illustrated in FIG. 3 is introduced to the desired site of deployment within a patient in the usual manner. The sheath retaining the stent graft in its compressed configuration is withdrawn, which allows the central section of the stent graft to expand as described above. The stent graft is restrained by a dual trigger-wire release mechanism, and this embodiment of the handle could be used to deploy the proximal end of the stent graft before the distal end of the stent graft. The proximal trigger wire is attached to the second bushing 93, whereas the distal trigger wire 43 is attached to the first bushing 193 within the rotatable portion 120 of the handle.

The first stage is for the surgeon to release the first safety screw 88. Once the first safety screw 88 has been removed, rotation of the rotatable section 82 of the rotatable portion 120 of the handle is possible. Rotation causes proximal movement of the first bushing 193 due to its engagement with the threading 90. Rotation of the first bushing 193 itself is prevented by its engagement with the second safety rod 294, along which it slides. Proximal movement of the first bushing 193 causes proximal movement also of the first safety rod 194 due to engagement of the shoulder 136 with the first bushing 193. The distal trigger wire is thus withdrawn, thereby releasing the distal end of the implant. The trigger wire constraining the bare stent 18 at the distal end of the implant is released, but the bare stent 18 is still retained within a cap covering the distal end of the stent graft.

The first bushing 193 can move in a proximal direction along the second safety rod 294 until it reaches the proximal shoulder 131 of the second safety rod 294, at which point further rotation of the rotatable section 82 of the rotatable portion 120 of the handle is prevented. This informs the surgeon that this stage of deployment (release of the distal end of the implant) has been completed.

Once the first safety rod 194 has been withdrawn from the aperture 150 of the second safety screw 188, it is possible for the surgeon to rotate the second safety screw 188, thereby removing it from engagement with the aperture 132 and the indentation 134. At this point, it is then possible to slide the slidable portion 122 of the handle over the middle portion 124 of the handle. The slidable portion 122 of the handle is attached to the cap covering the bare stent 18 at the distal end of the stent graft. Sliding the slidable portion 122 of the handle in a proximal direction thus results in uncovering of the bare stent 18 by causing proximal movement of the cover, enabling the bare stent 18 to expand and engage with the vessel wall.

On sliding the slidable portion 122 of the handle in a proximal direction the proximal shoulder 131 of the second safety rod 294 moves in a proximal direction relative to the first bushing 193. Since the first bushing 193 is no longer engaged with the proximal shoulder 131 of the second safety rod 294, further rotation of the rotatable section 82 of the rotatable portion 120 of the handle with respect to the stationary section 80 of portion 120 of the handle is enabled.

Upon further rotation of the rotatable portion 120 of the handle, the first bushing 193 once again moves in a proximal direction, eventually meeting the second bushing 93. As indicated above, the second bushing 93 is able to slide in a proximal direction when sufficient force (around 2.5 kg) is applied. Continued rotation of the rotatable section 80 of the handle causes the first bushing 193 to exert a force against the second bushing 93 in a proximal direction resulting in proximal movement of both bushings 93, 193. This movement can continue until the proximal face of the first bushing 193 once again abuts the shoulder 131 of the second safety rod 294.

The proximal movement of the second bushing 93 to which the proximal trigger wires are attached causes withdrawal of the proximal trigger wire attachment 50, and subsequent release of the proximal end of the implant. The proximal trigger wires are withdrawn into the deployment catheter; it is therefore unnecessary to discard of these separately.

The above-described embodiment provides several advantages. The handle itself prevents the surgeon from carrying out the deployment steps in an incorrect order.

Rotational movement of the handle is translated into axial movement of the bushings 93, 193. The rotational movement can prevent the generation of axial forces when initial withdrawal friction is overcome; the movement in the axial direction is therefore substantially smooth and continuous. This provides greater control of trigger wire withdrawal.

The trigger wires are withdrawn into the deployment catheter, which means they do not need to be separately removed: they can simply be removed from the patient at the same time as the deployment device.

The skilled person will appreciate that many modifications can be made to the above-described embodiment.

Figure 16:
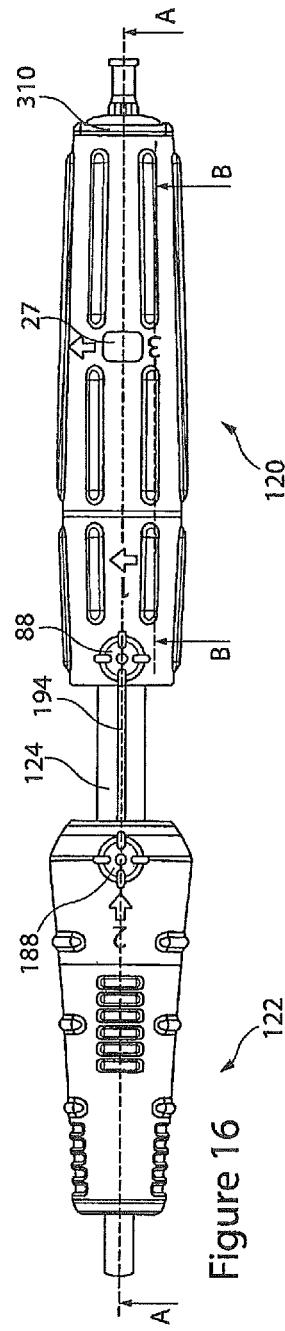
FIG. 16 is a top plan view of a modified version of the embodiment of FIGS. 12 to 15.
Figure 17:
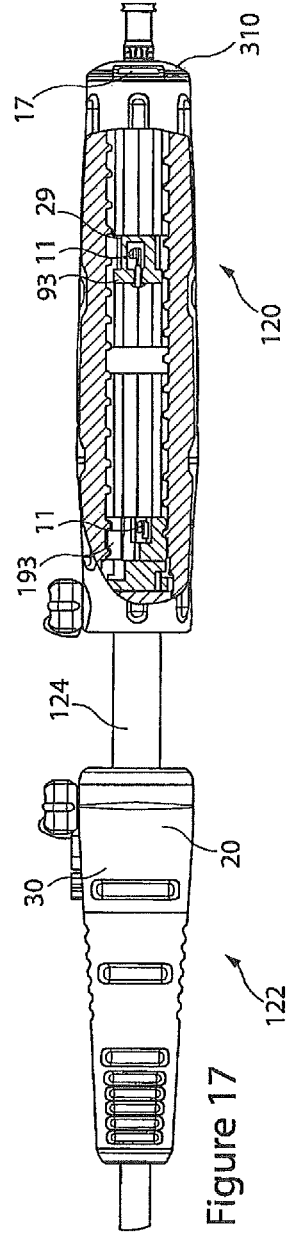
FIG. 17 is a view in partial cross-section of the handle of FIG. 16.
Figure 18:
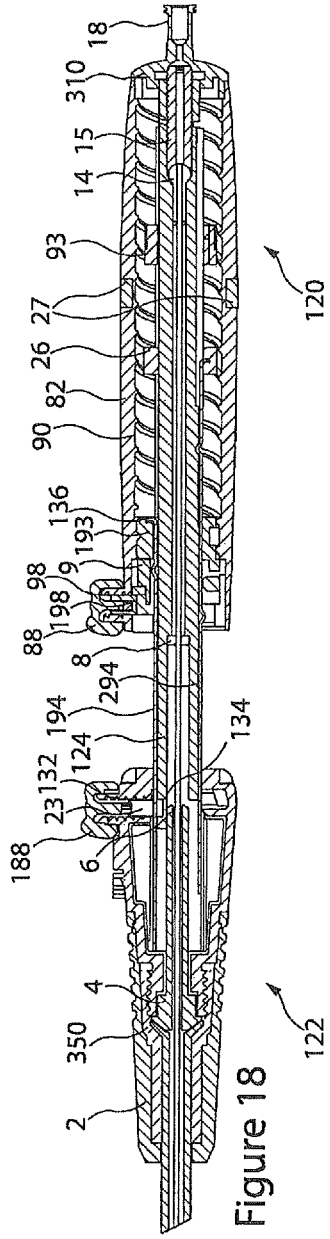
FIG. 18 shows a longitudinal cross-section of the handle of FIG. 16.

FIGS. 16 to 18 illustrate a modified version of the embodiment of the handle illustrated in FIGS. 12 to 15. It can be seen from FIGS. 16 to 18 that the handle is similar in many respects. However, this modified version includes many additional features, which may be combined and/or interchanged with features of the handle illustrated in FIGS. 12 to 15 (and in certain respects with the embodiment of the handle illustrated in FIGS. 8 to 11) as appropriate.

As above, the handle includes a rotatable portion 120 and a slidable portion 122. A middle portion 124 is provided between the rotatable portion 120 and the slidable portion 122. The function of the modified version of the handle illustrated in FIGS. 16 to 18 is largely the same as that of the handle illustrated in FIGS. 12 to 15, and will be described in detail below. There now follows, however, a detailed description of some of the specific features of the version of the handle illustrated in FIGS. 16 to 18.

Figure 19:
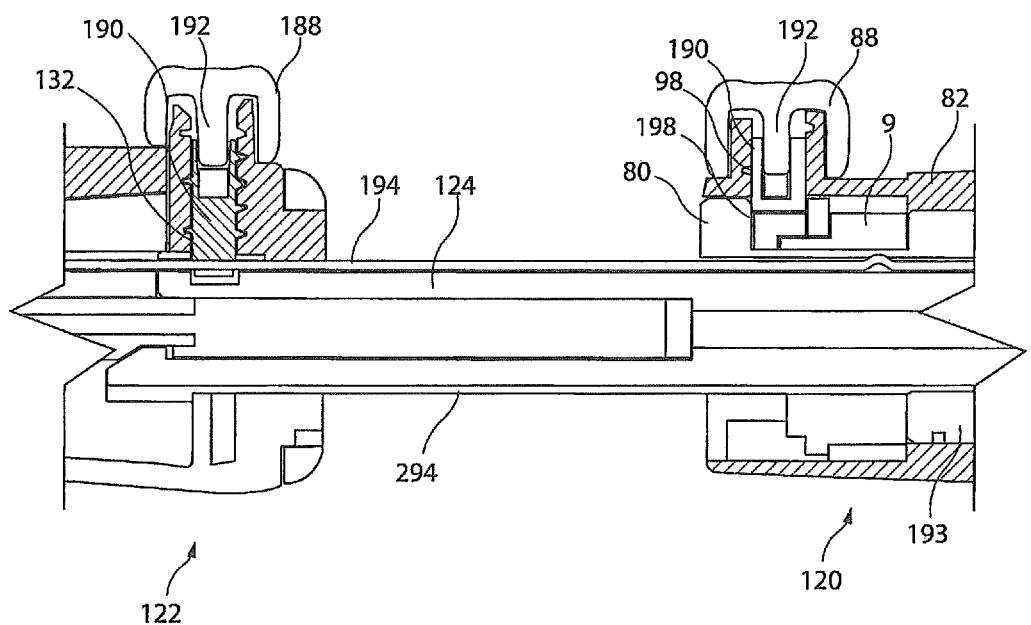
FIG. 19 shows a longitudinal cross-section of a portion of the handle of FIGS. 16 to 18.
Figure 20:
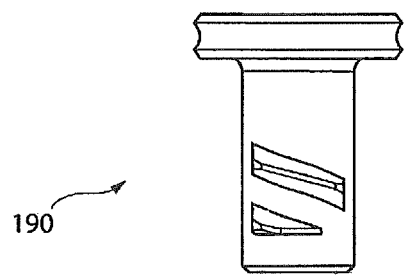
FIG. 20 is a side view of a component illustrated in FIG. 19.
Figure 21:
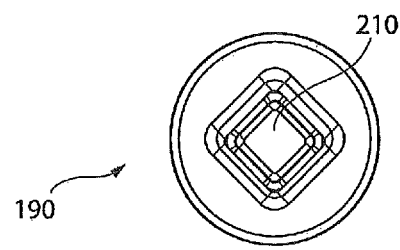
FIG. 21 is a top plan view of the component of FIG. 20.

FIG. 19 illustrates the first safety screw 88 and the second safety screw 188. The safety screws 88, 188 each include a post 192, each of which engages with a respective locking pin rotation member 190. The locking pin rotation member can be seen in more detail in FIGS. 20 and 21. The post 192 has a square cross-section, which fits within a square cross-section recess 210 within the locking pin rotation member 190. The locking pin rotation members 190 extend through the apertures 98, 198 provided between the stationary section 80 and the rotatable section 82 of the rotatable portion 120 of the handle for the first safety screw 88, and through the aperture 132 within the region of overlap between the slidable portion 122 and the middle portion 124 for the second safety screw 188. The locking pin rotation member 190 for the second safety screw 188 extends into the indentation 134 provided in the middle portion 124 of the handle, and also engages with the first safety rod 194, as can best be seen in FIG. 19. The locking pin rotation members 190 include an external screw thread that engages with an internal screw thread within the apertures 98, 132.

The thumb screws illustrated in FIG. 19 may be twisted 180 degrees in order to be released (in this embodiment the second safety screw 188 cannot be twisted until the first safety rod 194 has been withdrawn out of engagement with the locking pin rotation member 190). Twisting of the thumb screw 88, 188 causes corresponding rotation of the locking pin rotation member 190, which by engagement of the screw threads is caused to be moved outwardly from recess 210 of the locking pin rotation member 190. This unlocks the rotatable section 82 from the stationary section 80 of the rotatable portion of the handle with respect to the first safety screw 88. Release of the second safety screw 188 has the effect of unlocking the slidable portion of the handle 122 from the middle portion of the handle 124. An advantage of this modification is that rotating the thumbscrew by 180 degrees is sufficient for release. The thumbscrew does not need to be completely removed, and so a surgeon does not need to find somewhere to dispose of a removed thumbscrew.

Figure 22:
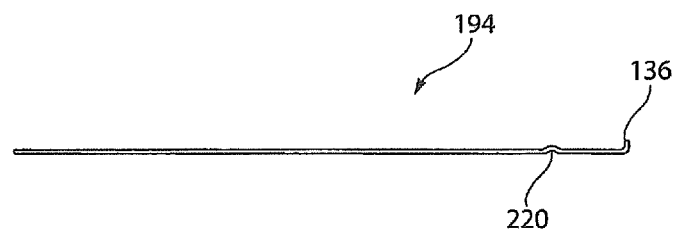
FIG. 22 is a side view of a component of the handle of FIGS. 16 to 18.
Figure 23:
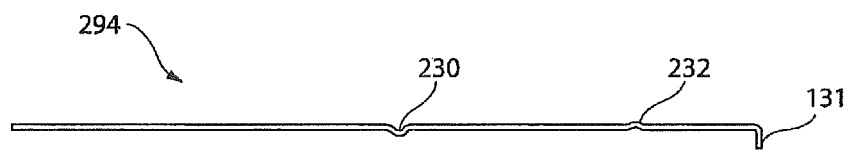
FIG. 23 is a side view of a component of the handle of FIGS. 16 to 18.
Figure 27:
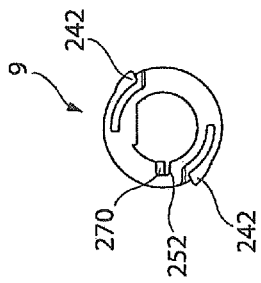
FIG. 27 is a view of the other end of the component of FIG. 24.
Figure 26:
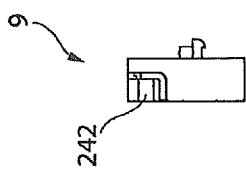
FIG. 26 is a view from the opposite side of the component of FIG. 24.
Figure 25:
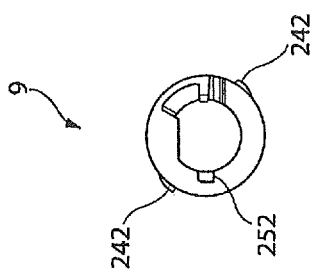
FIG. 25 is a view of one end of the component of FIG. 24.
Figure 24:
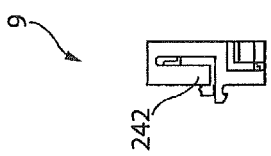
FIG. 24 is a side view of a component of the handle of FIGS. 16 to 18.

The first safety rod 194 and the second safety rod 294 are illustrated in more detail in FIGS. 22 and 23. The first safety rod 194 includes a proximal shoulder 136 and a radially outwardly protruding portion 220 (or bump) that acts as a positioning locator. The shoulder 136 engages with the proximal face of the first bushing 193.

The second safety rod 294 includes a shoulder 131 at its proximal end, which engages with a green-coloured marker ring 26. The second safety rod 294 also includes a radially outwardly extending protrusion 230 (or bump) approximately half way along its length, and a radially inwardly extending protrusion 232 between the shoulder 131 and the radially outwardly extending protrusion 230. The radially outwardly extending protrusion 230 is able to provide a "stop" function in conjunction with a rotation lock 9 (described in more detail below). The radially inwardly extending protrusion 232 acts as a positioning locator.

A locking ring 9 is provided within the rotatable portion 120 of the handle. The locking ring 9 is in the form of a bushing surrounding the longitudinal portion 86 of the stationary section 80 of the rotatable portion 120 of the handle. It is located at the most distal end of the rotatable section 120 of the handle, distally of the first bushing 193. The rotation lock 9 includes outwardly extending flaps 242. The flaps 242 extend radially outwardly at a shallow angle in the same direction. They are, however, resilient. It can therefore be seen that by providing corresponding abutments extending radially inwardly from the inner wall of the rotatable section 82 of the handle, rotation in one direction only of the rotatable section 82 of the handle around the rotation lock 9 is allowed, whilst rotation in other direction is prevented. Rotation of the rotation lock 9 itself within the rotatable portion 120 of the handle is prevented by provision of a flat surface on the longitudinal portion 86 of the stationary section 80 of the rotatable portion 120 of the handle and a corresponding flat surface on the inner wall of the locking ring 9.

The locking ring 9 also includes a groove 252 through which the second safety rod 294 extends. Within the groove 252 there is provided a chamfered projection 270, which can provided a stop for the second safety rod 294 in conjunction with the radially outwardly extending protrusion 230 of the second safety rod 294.

As indicated above, the shoulder 131 of the second safety rod 294 engages with a marker ring 26. The marker ring 26 is illustrated in more detail in FIGS. 28 and 29. In the preferred embodiment, the marker ring is coloured green, for reasons which will be explained below.

Figures 28, 29:
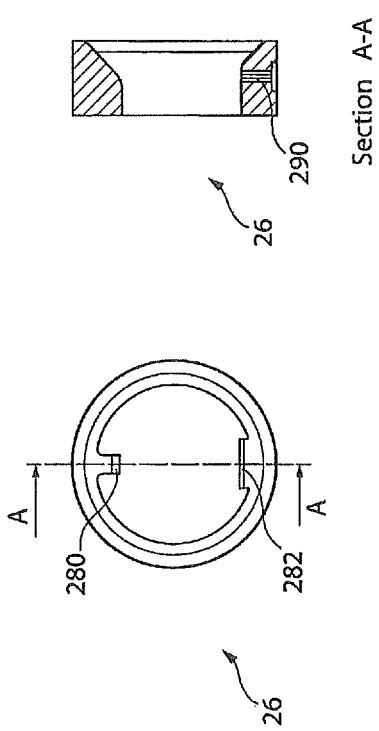
FIG. 28 is a view of an end of a component of the handle of FIGS. 16 to 18.
FIG. 29 is a cross-sectional view of the component of FIG. 28.

The marker ring 26 is located within the rotatable portion 120 of the handle distally of the second bushing 93, but proximally of the first bushing 193. Similarly to the second bushing 93, the marker ring 26 does not contain any external threading, and therefore does not move when the rotatable section 82 of the rotatable portion 120 of the handle is rotated. As can be seen in FIG. 28, the inner wall of the marker ring 26 includes a radially inwardly projecting element 280. This engages with a groove running along the longitudinal section 26 of the stationary section 80 of the rotatable portion 120 of the handle, and also a flat surface 282 that engages against a flat surface 282 of the longitudinal section 86 of the stationary section 80 of the rotatable portion 120 of the handle. The projection 280 and the flat surface 282 together prevent the marker ring 26 from rotating when the rotatable portion 82 of the handle is rotated. The marker ring includes a recess 290 (best seen in FIG. 29). The shoulder 131 of the second safety rod 294 engages with the recess 290.

Figure 30:
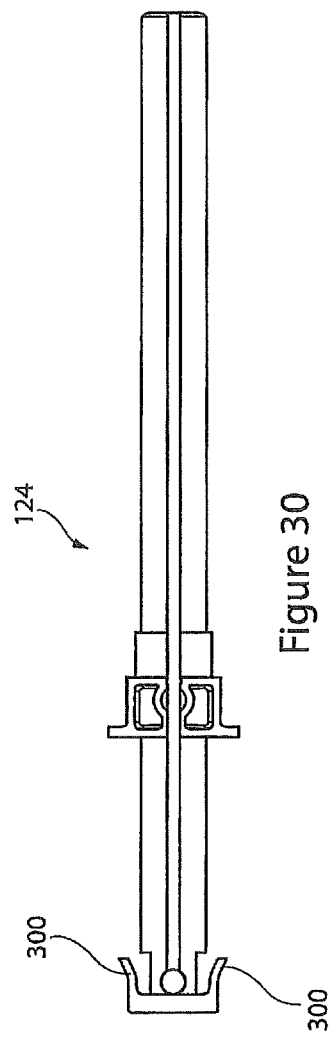
FIG. 30 is a side view of a component of the handle of FIGS. 16 to 18.

FIG. 30 illustrates the middle portion 124 of the handle in more detail. The middle portion 124 can be considered a sliding rod extending from the distal end of the rotatable portion 120 of the handle. As can best be seen in FIG. 18, the distal end of the middle portion 120 extends partially into a lumen of the slidable portion 122 of the handle. Once the second safety screw 188 has been released, the slidable portion 122 of the handle is able to slide over the middle portion 124 of the handle. The middle portion 124 of the handle includes at its distal end projections 300 that extend radially outwardly and proximally. These are able to engage with a recess provided in the lumen of the slidable portion 122 of the handle for the reasons described below.

FIGS. 31 to 33 illustrate a proximal end cap provided at the proximal end of the rotatable portion 120 of the handle. The proximal end cap 310 is held to the rotatable portion 120 of the device by a retainer clip (not shown). The retainer clip can be removed manually by the surgeon or clinician thereby to remove the proximal end cap 310. This allows the rotatable portion 120 of the handle to be removed, and allows manual removal of the trigger wires. This quick-release mechanism provides a manual by-pass to the handle mechanism by which the elements of the assembly can be withdrawn by pulling in the axial (proximal) direction in a manner analogous to traditional introducer assemblies. This is useful in cases where complications arise during the medical procedure and where it is necessary to effect rapid deployment or removal of the medical device. Whilst such an emergency deployment procedure is inferior to correct deployment using the handle, it allows the implant to be deployed or removed without resorting to an open is vessel procedure, which may be necessary should such problems arise during deployment using currently known handles.

Figure 34:
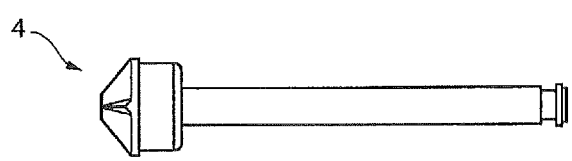
FIG. 34 is a side view of a component of the handle of FIGS. 16 to 18.
Figure 35:
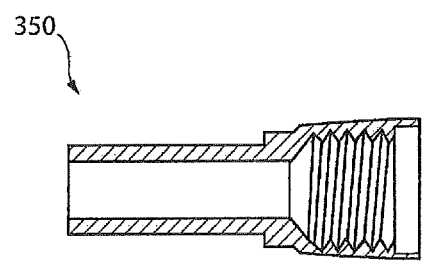
FIG. 35 shows a longitudinal cross-section of a component of the handle of FIGS. 16 to 18.
Figure 36:
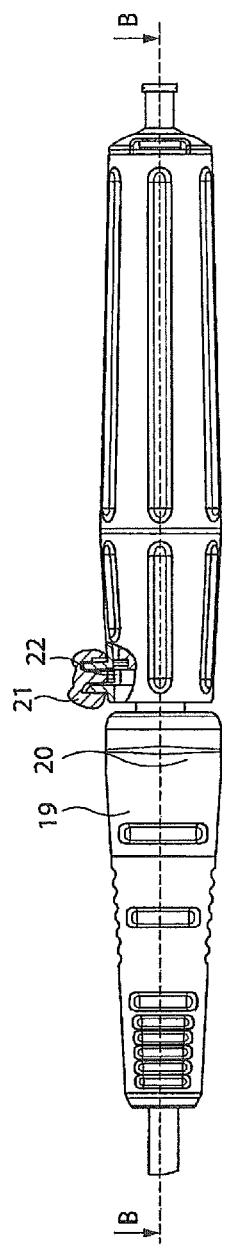
FIG. 36 is a perspective view from the side (partially in cross-section) of a modified version of the handle of FIGS. 8 to 11.

The slidable portion 122 of the handle includes a sealing rod 4 and a sealing cap 350. These can be seen in more detail in FIGS. 34 and 35. The sealing rod 4 extends from the distal end of the middle portion 124 of the handle, but is able to slide within a lumen of the middle portion 124 of the handle. The distal end of the sealing rod 4 engages within the sealing cap 350.

The wall of the rotatable section 82 of the rotatable portion 120 of the handle includes a window 27. This allows the user to see when the green coloured marker ring 26 is aligned with the window as described below.

In use, as with the handle illustrated in FIGS. 12 to 15, it is to be noted that the second safety screw 188 cannot be rotated at the beginning of the deployment procedure because it is engaged with the first safety rod 194. Therefore, the first step is for the surgeon or clinician to rotate by 180 degrees the first safety screw 88. As described above with reference to FIG. 19, this results in the locking pin rotation member 190 disengaging from the aperture provided in the stationary section 80 of the rotatable portion 120 of the handle. It is then possible to rotate the rotatable section 82 of the rotatable portion 120 of the handle.

As the rotatable section 82 of the rotatable portion 120 of the handle is rotated, the first bushing 193 moves in a proximal direction within the rotatable portion 120 of the handle. This is due to engagement of its external threading with the internal threading provided in the rotatable portion 120 of the handle. As the first bushing 193 moves in a proximal direction, the first safety rod 194, which is engaged by means of the shoulder 136 with the first bushing 193 is also withdrawn in a proximal direction. At the same time, trigger wires attached to the first bushing 193 and constraining the distal bare stent 18 are withdrawn in a proximal direction thereby releasing the distal bare stent 18.

Continued rotation of the rotatable section 82 of the rotatable portion 120 of the handle causes continued proximal movement of the first bushing 193. This proximal movement continues until the first bushing 193 meets the marker ring 26. When the first bushing 193 meets the marker ring 26, continued rotation of the rotatable section 82 of the rotatable portion 120 of the handle causes proximal movement also of the marker ring 26. As the marker ring 26 moves in a proximal direction, the second safety rod 294 is also moved in a proximal direction. Eventually, the radially outwardly extending protrusion 230 meets the chamfered portion 252 provided on the rotation lock 9 to lock together acting to prevent rotation of the handle.

The proximal movement of the first bushing 193 and the first safety rod 194 is such that the first safety rod 194 is now disengaged from the locking pin rotation member 190 corresponding to the second safety screw 188. The second safety screw 188 can thus now be rotated 180 degrees in order to disengage the locking pin rotation member 190 from the indentation 134 provided on the middle portion 124 of the handle. The slidable portion 122 of the handle can then slide over the middle portion 124 of the handle to withdraw the cap within which the bare stent 18 is constrained.

Once the middle portion 124 has slid into the lumen of the slidable portion of the handle 122 approximately to its full extent, the projections 300 at the proximal end of the middle portion 124 of the handle engage with the recesses provided in the lumen of the slidable portion 122 of the handle, thereby preventing distal movement of the slidable portion 122 of the handle. This ensures that sliding of the slidable portion 122 of the handle in a proximal direction is irreversible.

Once the slidable portion 122 of the handle has moved proximally to its full extent, it is once again possible to rotate the rotatable section 82 of the rotatable portion 120 of the handle. This is because proximal movement of the slidable portion 122 of the handle causes engagement between the distal end of the second safety rod 294 and the distal end of the lumen provided in the slidable portion 122 of the handle. The distal end of the lumen pushes against the distal end of the second safety rod 294 in a proximal direction, thereby causing proximal movement of the second safety rod 294. This proximal movement causes the radially outwardly extending projection 230 to overcome the resistance provided by the chamfered portion 252 of the locking ring 9, thereby allowing further rotation of the rotatable portion 120 of the handle. As the slidable portion 122 of the handle is pulled back in a proximal direction, the outwardly extending protrusion 230 is pushed in a proximal direction, thus allowing further rotation of the locking ring 9.

Further rotation of the rotatable section 82 of the rotatable portion 120 of the handle results in further proximal movement of the first bushing 193, and of the marker ring 26 against which it now abuts. Eventually, the first bushing 193 and the marker ring 26 meet the second bushing 93, to which the proximal trigger wire is attached.

At this point, the green marker ring 26 is located in line with the window 27 in the wall of the rotatable section 82 of the rotatable portion 120 of the housing. This signifies that continued rotation of the rotatable portion 120 of the handle will result in release of the proximal trigger wires. Continued rotation of the rotatable section 82 of the rotatable portion 120 of the handle causes proximal movement of the second bushing 93, and therefore withdrawal of the proximal trigger wire attached to the second bushing 93 and release of the proximal end of the implant.

Figure 37:
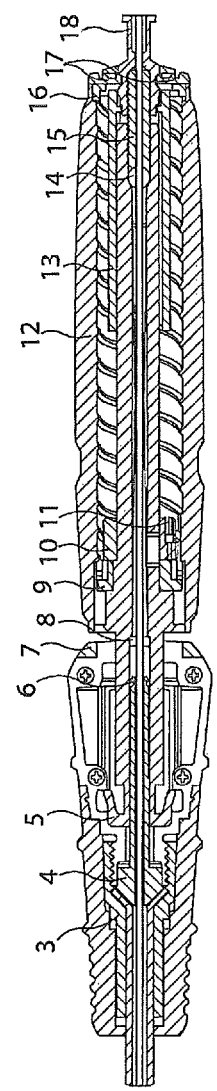
FIG. 37 shows a longitudinal cross-section of the handle of FIG. 36.

FIG. 37 is a modified version of the handle illustrated in FIGS. 8 to 11. It can been seen also, that this version of the handle resembles the version illustrated in FIGS. 6 to 18, whereby the slidable portion has simply been locked in its most proximal position.

The handle could also be modified to withdraw also a sheath covering an implant. This could be achieved in a variety of ways, such as by providing at the proximal end of the sheath one or more wires or tabs which couple to the handle mechanism or by changing the design of the handle mechanism to engage and pull the sheath itself. Such modifications will be within the ability of a person of average skill in the art.

Figure 38:
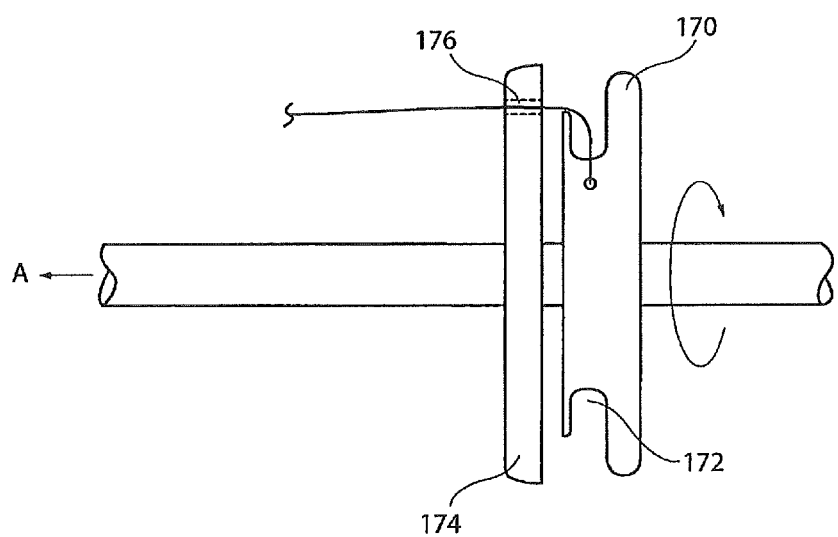
FIG. 38 is a side view of a portion of a third embodiment of a handle.

FIG. 38 illustrates an embodiment of spool arrangement for winding a trigger wire as this is pulled proximally during deployment. The arrangement includes a spool element 170 that is substantially circular in shape. The spool element 170 is arranged to rotate with the handle mechanism when the latter is rotated. The spool element 170 has attached thereto the proximal end of a trigger wire to be withdrawn. The spool element 170, in this embodiment, includes a groove 172 around its circumference. The purpose of this will be described below.

A support member 174 is located just distally of the spool element 170 and is rotatably fixed. The support member 174 includes a hole 176 passing therethrough which is generally radially aligned with the spool element 170. The trigger wire 40 to be withdrawn passes through the aperture 176 of the support member 174.

When the handle assembly is actuated, the spool element 170 rotates, pulling the trigger wire with it, the latter being wound into the groove or channel, being fed into position by the relatively stationary hole 176.

An advantage of the above-described embodiment is that the trigger wire can be fully withdrawn into the handle. It therefore does not need to be removed separately.

Various modifications to the embodiments described above may be substituted for or combined with one another as desired. It is also to be understood that the various features of the dependent claims appended hereto may be used with one another in any desired or appropriate combination of those claims.

The disclosure in the abstract accompanying this application is incorporated herein by reference.

What is claimed is:
1. A handle for an implant deployment device including:
a rotatable member;
a trigger wire attachable to an implant;

a first trigger wire release mechanism movable to withdraw the trigger wire from a portion of an implant;
the trigger wire attached to the first trigger wire release mechanism,
a slidable portion releasably engaged with the first trigger wire release mechanism and axially aligned with the rotatable member and located distally of the rotatable member, the slidable portion movable in a proximal direction towards the rotatable member;
wherein rotation of the rotatable member moves the first trigger wire release mechanism in the proximal direction to withdraw the trigger wire from a portion of an implant, and wherein the slidable portion is only movable in the proximal direction towards the rotatable member after movement of the first trigger wire release mechanism in the proximal direction.

2. A handle as claimed in claim 1, wherein the first trigger wire release mechanism is movable in the proximal direction with respect to the handle, the first trigger wire release mechanism being engaged with the rotatable member such that upon rotation of the rotatable member the first trigger wire release mechanism moves in the proximal direction with respect to an implant deployment device.

3. A handle as claimed in claim 2, wherein the trigger wire attachable to an implant is attached to the first trigger wire release mechanism, such that movement of the first trigger wire release mechanism in the proximal direction results in withdrawal of the trigger wire.

4. A handle as claimed in claim 2, wherein the rotatable member is substantially cylindrical and includes an internal lumen and an internal screw thread, wherein the first trigger wire release mechanism comprises a substantially cylindrical bushing located within the internal lumen of the rotatable member, the bushing includes an external screw thread engaged with the internal screw thread of the rotatable member, and wherein the first trigger wire release mechanism also comprises a longitudinal member that engages and extends through the bushing to prevent rotation thereof when the rotatable member is rotated.

5. A handle as claimed in claim 2, wherein a stop is provided so as to allow movement of the first trigger wire release mechanism for a limited distance in the proximal direction.

6. A handle as claimed in claim 1, including a first releasable lock operable to prevent rotation of the rotatable member.

7. A handle as claimed in claim 6, wherein the first releasable lock is operable to fix the rotatable member to a non-rotatable portion of the handle in order to prevent rotation of the rotatable member.

8. A handle as claimed in claim 1, wherein a stop is provided so as to allow movement of the first trigger wire release mechanism for a limited distance in the proximal direction and wherein the slidable portion is only movable in the proximal direction after the first trigger wire release mechanism has moved by said limited distance.

9. A handle as claimed in claim 8, wherein the movement of the slidable portion in the proximal direction disengages the stop, thereby allowing the trigger wire release mechanism to move longitudinally in the proximal direction.

10. A handle as claimed in claim 9, wherein the slidable portion is only movable in the proximal direction towards the rotatable member after movement of the first trigger wire release mechanism in the proximal direction.

11. A handle as claimed in claim 10, wherein a second trigger wire release mechanism is arranged to move longitudinally in the proximal direction only after the stop has been disengaged.

12. A handle as claimed in claim 11, wherein the first trigger wire release mechanism is able to exert a force in the proximal direction on the second trigger wire release mechanism in order to cause the second trigger wire release mechanism to move in the proximal direction.

13. A handle as claimed in claim 10,
wherein the rotatable member is substantially cylindrical and includes an internal lumen and an internal screw thread,
wherein the first trigger wire release mechanism comprises a substantially cylindrical bushing located within the internal lumen of the rotatable member and the bushing includes an external screw thread engaged with the internal screw thread of the rotatable member,
wherein the first trigger wire release mechanism also comprises a longitudinal member that engages and extends through the bushing to prevent rotation thereof when the rotatable member is rotated, and wherein a second trigger wire release mechanism is substantially cylindrical and is located within the internal lumen of the rotatable member proximal of the first trigger wire release mechanism, and
wherein the second trigger wire release mechanism does not include an external screw thread engaged with the internal screw thread of the rotatable member.

14. A handle as claimed in claim 1, including a releasable lock operable to prevent longitudinal movement of the slidable portion.

15. A handle as claimed in claim 14, wherein the releasable lock is operable to fix the slidable portion to a non-slidable portion of the handle in order to prevent longitudinal movement of the slidable portion.

16. A handle as claimed in claim 15,
wherein a stop is provided so as to allow movement of the first trigger wire release mechanism for a limited predetermined distance in the proximal direction and wherein the releasable lock can only be released after the first trigger wire release mechanism has moved by said limited predetermined distance.

17. A handle as claimed in claim 16, wherein the releasable lock engages with the slidable portion of the handle and with the non-slidable portion of the handle thereby preventing relative movement therebetween, wherein the first trigger wire release mechanism includes a bushing and a longitudinal member attached to the bushing, wherein the releasable lock engages with the longitudinal member such that the releasable lock cannot be released whilst engaged with the longitudinal member, whereby movement of the first trigger wire release mechanism in the proximal direction causes disengagement of the longitudinal member from the releasable lock.

18. An implant deployment device including a handle as claimed in claim 1.

19. A handle for an implant deployment device including:
a rotatable member;
a slidable portion releasably engaged with a first release mechanism and axially aligned with the rotatable member and located distally of the rotatable member, the slidable portion movable longitudinally towards the rotatable member, the rotatable member movable independently of the slidable portion;
the first release mechanism engaged with the rotatable member and movable to release an implant;
a lock releasably locking the slidable portion, preventing longitudinal movement thereof;

wherein rotation of the rotatable member causes the first release mechanism to release an implant and allow the lock to release from the slidable portion; and wherein the slidable portion is only movable longitudinally towards the rotatable member after the lock is released.

* * * * *